(12) United States Patent
Coyne et al.

(10) Patent No.: US 7,045,365 B2
(45) Date of Patent: May 16, 2006

(54) SUPPORTED ALDEHYDIC SILANES AND METHOD OF MANUFACTURE

(75) Inventors: Ann N. Coyne, Voorhees, NJ (US);
John H. MacMillan, Ambler, PA (US);
Michael J. Telepchak, Yardley, PA (US)

(73) Assignee: United Chemical Technologies Inc., Bristol, PA (US)

( * ) Notice: Subject to any disclaimer, the term of this patent is extended or adjusted under 35 U.S.C. 154(b) by 446 days.

(21) Appl. No.: 10/438,432

(22) Filed: May 15, 2003

(65) Prior Publication Data

US 2003/0207468 A1 Nov. 6, 2003

Related U.S. Application Data

(62) Division of application No. 09/847,212, filed on May 2, 2001, now Pat. No. 6,589,799.

(51) Int. Cl.
| | |
|---|---|
| G01N 33/552 | (2006.01) |
| G01N 33/553 | (2006.01) |
| G01N 33/545 | (2006.01) |
| G01N 33/548 | (2006.01) |
| C07K 17/08 | (2006.01) |
| C07K 17/10 | (2006.01) |
| C07K 17/14 | (2006.01) |

(52) U.S. Cl. ............ 436/527; 435/7.92; 436/525; 436/526; 436/529; 436/531; 530/391.1; 530/410

(58) Field of Classification Search .......... 436/527, 436/525, 531, 529, 526; 435/7.92; 530/391.1, 530/410

See application file for complete search history.

(56) References Cited

U.S. PATENT DOCUMENTS

| 4,377,555 A | * | 3/1983 | Hancock et al. ............ 423/6 |
| 4,384,045 A | * | 5/1983 | Ho et al. .................. 435/176 |
| 4,506,015 A | * | 3/1985 | Ho et al. .................. 435/175 |
| 4,894,468 A | * | 1/1990 | Wilchek et al. ............ 556/416 |
| 5,625,055 A | * | 4/1997 | Caddy et al. ............ 536/25.42 |

FOREIGN PATENT DOCUMENTS

| FR | 2 435 715 A | | 4/1980 |
| FR | 2435715 | * | 4/1980 |

OTHER PUBLICATIONS

Bruning, C., et al. *Aldehyde-functionalized Ethozysilanes as a New Enzyme Immobilization Reagents.* J. Chem Soc., Chem Commun. 1995, pp. 2323-2324, especially Fig. 1and p. 2323, first through third full paragraphs.

Borchert, A., et al. *High-Performance Liquid Affinity Chromatography on Silica-Bound Concanavalin A.* Journal of Chromatography. 1982, vol. 244, pp. 49-56, Fig. 1.

* cited by examiner

*Primary Examiner*—Mary E. Ceperley
(74) *Attorney, Agent, or Firm*—Robert A. Koons, Jr.; Matthew P. McWilliams; Drinker Biddle & Reath LLP

(57) ABSTRACT

A method for producing a derivatized aldehydic support matrix material includes activating surface hydroxyl groups on the support matrix material and reacting the activated hydroxyl groups with an aldehydic alkoxy silane. The derivatized aldehydic support matrix material produced is useful for immobilizing bio-molecules in biological applications.

15 Claims, No Drawings

SUPPORTED ALDEHYDIC SILANES AND METHOD OF MANUFACTURE

RELATED APPLICATION DATA

This application is a Divisional of U.S. application Ser. No. 09/847,212 filed on May 2, 2001 now U.S. Pat. No. 6,589,799.

FIELD OF THE INVENTION

The present invention relates generally to derivatized solid supports. More particularly, the present invention relates to solid supports derivatized with silanes containing aldehydic functionalities and their use in biological applications.

BACKGROUND OF THE INVENTION

The use of immobilized bio-molecules is an essential technique required for many biological applications. A common method used to immobilize bio-molecules is by reaction of the primary amine groups of the biological molecules with an aldehyde functionality that is bonded to a solid support matrix.

A popular method of introducing aldehydes to the solid support matrix is through the activation of an amine-functionalized surface with a glutaraldehyde solution. Although popular, this method has several disadvantages. First glutaraldehyde is an unstable compound that is difficult to purify. Additionally, two Schiff bases are present in the covalent linkage of the bio-molecule to the support. Additionally, the Schiff base linkage of the glutaraldehyde to the support is susceptible to hydrolysis and thus may lead to ligand leaching. Treatment with a reducing agent such as sodium borohydride or sodium cyanoborohydride to remove the Schiff bases can be performed, but this adds an additional step to the process.

There remains a need for a solid support matrix with bonded aldehydic functionalities for immobilizing bio-molecules that is stable and can be produced in a simple process.

Accordingly, it is desirable to provide a solid support matrix containing bonded aldehydic functionalities that is stable and can be used to immobilize bio-molecules. It is further desirable to provide a simple method for producing such a solid support matrix. It is still further desirable to provide an apparatus and method for using a solid support matrix with aldehydic functionalities to immobilize bio-molecules for biological applications.

SUMMARY OF THE INVENTION

The present invention is directed to a derivatized solid support matrix containing bonded aldehydic functionalities, that is stable and can be used to immobilize bio-molecules, as well as to a method for producing such a derivatized solid support matrix.

The present invention is further directed to an apparatus and method for using a derivatized solid support matrix with aldehydic functionalities to immobilize bio-molecules for biological applications.

In accordance with one embodiment of the present invention, a method of producing a derivatized matrix material with aldehyde groups is provided. A raw support matrix material having a surface area with hydroxyl groups occurring on the surface area is activated with an acid. The activated support material is then exposed to an alkoxy aldehydic silane to produce a derivatized matrix material. The support matrix material can be selected from a number of materials, including but not limited to glasses, agarose, silica, alumina, glass-coated ELISA plates, resin, nickel, aluminum, zinc and paramagnetic iron. The support matrix material may have naturally occurring hydroxyl groups, or the hydroxyl groups may be introduced artificially. A number of mono, di and tri alkoxy aldehydic silanes may be used for producing a derivatized matrix material with aldehyde groups. The alkoxy aldehydic silane is preferably a trialkoxy aldehydic silane.

In another embodiment of the present inventions, an aldehydic derivatized matrix material comprises a support matrix material having a surface area, and a siloxane coating is disposed on at least a portion of the surface area. The siloxane coating may be a mono-layer or a cross linked siloxane polymer coating. The siloxane coating has a plurality of organic substituents containing aldehydic functional groups pendant therefrom. The organic substituents are bound to the siloxane coating via carbon-silicon covalent bonds.

In accordance with another embodiment of the invention, the aldehydic derivatized support matrix material can be incorporated into an apparatus for immobilizing bio-molecules for biological applications. Such biological applications include, but are not limited to, combinatorial chemistry, molecular biology, ELISA (Enzyme-Linked Immunosorbent Assay) plates, and cell sorting and identification.

There are additional features of the invention that will be described below and which will form the subject matter of the claims appended hereto.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

One aspect of the present invention provides a composition comprising a derivatized solid support matrix material having a surface and a siloxane coating on at least a portion of its surface, linked through Si—O bonds. The siloxane coating comprises a plurality of silicon atoms that are either individually mono-linked to the solid support matrix or cross-linked to each other and further bonded to the support matrix through Si—O bonds to form a siloxane polymer. Each Si unit in the coating has a pendant aldehyde containing organic substituent, bound to the siloxane coating via carbon-silicon covalent bonds. The siloxane coating is further bound to the solid support matrix material through Si—O—M bonds, wherein M is the support matrix material.

According to one embodiment of the composition, the siloxane coating comprises a multi layer siloxane polymer 1 to 10 Si units deep, preferably 2 to 5 units deep. When viewed in cross section, this embodiment has the general structure:

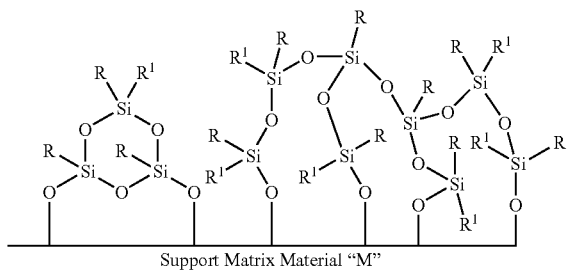

where R is an aldehyde containing organic substituent. $R^1$ is $C_1$ to $C_{30}$ alkyl, $C_1$ to $C_{30}$ alkenyl, phenyl, naphthyl or hydrogen, and M is the support matrix material. It should be recognized that in this embodiment the placement of the individual Si units is random with respect to the support matrix material. The example given is for illustrative purposes only and is not meant to limit the scope of the invention.

In an alternate embodiment, the individual Si units are cross linked to form a siloxane polymer 1 Si unit deep, which when viewed in cross section, has the structure:

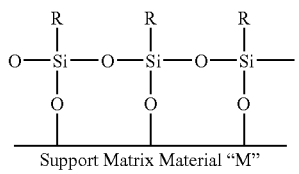

where R is an aldehyde containing organic substituent and M is the support matrix material.

In a further embodiment, the individual Si units are mono linked to the solid support matrix material, which when viewed in cross section would have the structure:

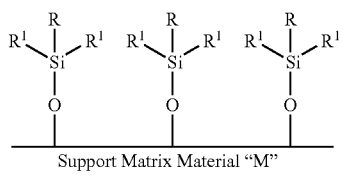

where R is an aldehyde containing organic substituent. $R^1$ is alkyl or alkenyl containing 1 to 30 carbon atoms, phenyl, naphthyl or hydrogen and M is the support matrix material.

The aldehyde containing organic substituent, R, may be a straight chain, branched or cyclic alkane containing from 1 to 30 carbon atoms. Alternatively, R may be aromatic or some other unsaturated aldehyde-containing hydrocarbon. For example, wherein R is formaldehyde, a single layer polymer coating would have the following structure when viewed in cross section:

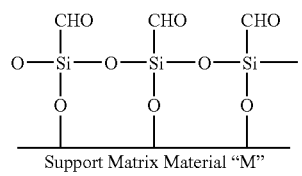

In an alternative embodiment the aldehydic organic substituents pendant from the Si units may vary between the individual Si units, as shown by:

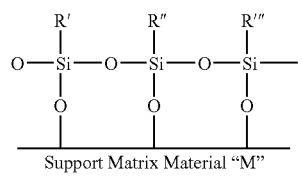

where R', R" and R'" may all be different aldehyde containing organic substituents.

Suitable materials for the solid support matrix include, but are not limited to glasses, agarose, silica, alumina, glass-coated ELISA plates, resin, nickel, aluminum, zinc and paramagnetic iron. Preferably, the solid support matrix material comprises silica. The support matrix material may be granular or in the form of beads. The support may also be a glass, metal or ceramic slide, or granular or bead material supported on a glass, metal or ceramic slide.

Another aspect of the current invention provides a method for producing a derivatized matrix support material as described above. In this aspect of the invention, a raw solid support matrix material is provided. The raw solid support matrix material has hydroxyl groups occurring on its surface area. The hydroxyl groups may be naturally occurring or may be artificially introduced by methods well understood by those skilled in the art. Such methods include, but are not limited to treatment with aqueous base, plasma treatments or corona treatments. Preferably, the solid support matrix material is a silica gel.

The hydroxyl groups on the solid support matrix material may be activated using an acid. Preferably, a suspension of the matrix material is formed in an organic solvent and an aqueous acid is added to the suspension. Preferably the organic solvent is a non-polar solvent, such as hexanes or n-heptane. The acidified suspension is then mixed and allowed to equilibrate.

An aldehyde functionality is introduced via an alkoxy aldehydic silane. The alkoxy aldehydic silane may be a single species or mixture of species selected from the group having the general formulas:

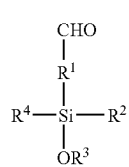

1

-continued

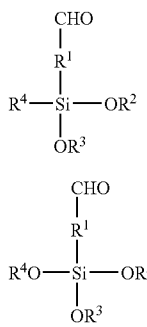

where $R^1$ is an alkyl or alkenyl containing 1 to 30 carbon atoms, a phenyl, a naphthyl, or is a covalent bond. $R^2$, $R^3$ and $R^4$ are independently alkyl or alkenyl containing 1 to 30 carbon atoms, phenyl, naphthyl, silyl or hydrogen. In a preferred embodiment, the alkoxy silane is a trialkoxy silane according to structure 3, and none of $R^2$, $R^3$ or $R^4$ is hydrogen. In a more preferred embodiment, $R^2$, $R^3$ and $R^4$ are equivalent. Preferred $R^2$, $R^3$ and $R^4$ groups are methyl, ethyl and propyl. Preferred $R^1$ groups are straight chain alkanes having 1 to 10 carbon atoms.

The alkoxy silane is added to the acidified suspension and allowed to react with the activated hydroxyl groups on the surface of the matrix material. Preferably, the alkoxy silane is added in small portions over a period of hours. Most preferably, there is an equilibration period between additions of the alkoxy silane. For example, 10 mL of aldehydic alkoxy silane may be added to a suspension of 30 grams of silica in 0.5 mL portions at intervals of 8 to 12 minutes over a period of 3 to 4 hours. Under the acidic conditions in the suspension, the alkoxy silane will be hydrolyzed, producing an alcohol and silanol for each alkoxy substituent, following the general formula:

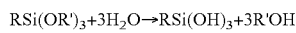

where R is the aldehyde containing organic substituent. The silanol thus produced can then react with the activated hydroxyl groups on the surface of the matrix material to produce the derivatized material. It will be recognized that the stoichiometry of the reaction will vary depending on alkoxy aldehydic silane employed.

Following addition of the alkoxy silane, the now derivatized matrix material is preferably collected and washed to remove excess acid, unbound silane and polymers.

It is recognized that a number of solid support matrix materials can be used alone, or in combination to achieve a derivatized material having desired qualities. It is also recognized that mixtures of alkoxy silanes having different aldehydic substituents can be used to produce a derivatized material having a wide variety of desired qualities.

The derivatized aldehydic material thus produced can be used as part of an apparatus for immobilizing bio-molecules for biological applications. In one embodiment of this aspect of the invention, a polypropylene column is used to contain an aldehydic derivatized support matrix material according to the current invention. The column is open at one end and has a porous bed support at the opposite end for supporting the matrix material, while allowing fluid to pass. An example of a column suitable for use in this embodiment is the POLY-PREP® conical polypropylene column, available from Bio-Rad Laboratories Inc.

In another embodiment of this aspect of the invention a column may be used that is compatible for use with a centrifuge. In this embodiment, separation of sample components is affected through centrifugal force. An example of a column suitable for use in this embodiment is the MICRO BIO-SPIN® chromatography columns, also available from Bio-Rad Laboratories Inc. However, it will be recognized that the invention is not limited to a particular brand of column or a particular design, shape or material of construction.

The apparatus as described in the embodiments above can be used to immobilize a wide variety of bio-molecules. The general procedure followed to immobilize a bio-molecule involves first washing the derivatized support matrix material contained in the column with a buffer solution of appropriate pH. The pH of the buffer solution will vary depending on the bio-molecule to be immobilized and the derivatized support matrix material being used. However, the pH of the buffer solution is preferably in the range of about 4 to about 10, more preferably from about 8 to about 10. A solution containing the bio-molecule to be immobilized is then added to the column in a buffer solution. The apparatus containing the bio-molecule solution is then incubated at an appropriate temperature, for a time sufficient to immobilize at least a portion of the bio-molecule contained in the solution. Again incubation temperatures and times will vary depending on the bio-molecule being immobilized and the derivatized support matrix material being used. Following the incubation period, the column is drained of solution and preferably washed at least once with a fresh buffer solution. Preferably, the buffer solution used is identical to the solution used to initially wash the column. Washing with buffer solution removes any unbound material from the column. The apparatus containing the immobilized bio-molecule may then be further derivatized or used in an assay as desired.

In another embodiment of this aspect of the invention, the support material is a glass coated ELISA (Enzyme-Linked Immunosorbent Assay) plate. In this embodiment, the test bio-molecule is attached covalently to the ELISA plate. A rapid test can then be performed, where an antibody or antigen is coupled to an enzyme as a means for detecting an antigenic match.

Other applications where the current invention may be employed include combinatorial chemistry; tethered amine modified oligonucleotides for PCR (Polymerase Chain Reaction); RNA isolation/purification; DNA micro arrays, probes and genome chips; cell sorting and identification.

The following examples demonstrate the method of producing a derivatized support material according to the current invention and a method of using the invention for immobilizing bio-molecules.

EXAMPLE 1

In a 250 mL beaker, 25 grams of raw 40–60 μm silica gel was suspended in 250 mL of hexanes. A solution of 0.30 mL of glacial acetic acid in 2.0 mL of water was then added to the suspension. The mixture was allowed to equilibrate by mixing for 30 minutes. Over a 2–3 hour period, 7.5 mL of triethoxy aldehydic silane was added to the suspension in 0.5 mL aliquots. After each addition, the suspension was purged with nitrogen and recovered. Following the additions, the suspension was allowed to mix for five hours. The silica was collected and washed with 600 mL of isopropyl alchohol and one 1 L of deionized water. The resulting aldehydic silica was stored in a glass container and immersed in $N_2$ purged deionized water under nitrogen at 4° C. This procedure was repeated three times.

EXAMPLE 2

The four derivatized aldehydic silicas produced in Example 1 were each analyzed in duplicate to quantify of polymeric coating on the silica. The organic loading of the silicas was determined using the following method. Samples of each of the four silicas produced in Example 1 were taken and dried under nitrogen at 103° C. for four hours and then cooled in a desiccator. The dried material was weighed and then ignited in a furnace at 950° C. Igniting the samples caused all of the organic material to be volatilized, leaving only $SiO_2$. The organic loading of the samples can be expressed as:

% organic loading=[1−(wt.ash/wt.sample)]×100 where "wt. sample" is the mass of the sample before ignition and "wt. ash" is the mass of the sample after ignition. A silica gel blank was also ignited under the same conditions as a control. The results are shown in TABLE 1.

TABLE 1

| Sample | Organic Loading Average of 2 trials |
|---|---|
| 1 | 8.20% |
| 2 | 8.13% |
| 3 | 8.23% |
| 4 | 8.29% |
| average | 8.21% |
| silica blank | 3.5% |

The overall average organic loading found on the derivatized silica produced in Example 1 is 8.21%, with a standard deviation of 0.067% and a coefficient of variation of 0.82%. In comparison, the silica gel blank showed a carbon loading of only 3.5%. These values demonstrate the successful attachment of the alkoxy aldehydic silane to the silica particles.

EXAMPLE 3

A bio-molecule, Protein A, available from Prozyme, Inc., was attached to the derivatized support material produced in Example 1 to demonstrate the activity of the silica surface as well as the loading capacity of the Protein A. The bio-molecule Protein A is available from a number of natural and artificial sources. The Protein A used in this example was produced from the enzyme *staphylococcus aureus*. A 0.4 mL sample of the aldehydic silica was added to a POLY-PREP® polypropylene fritted column, available from Bio-Rad. The material was then washed with 5 columns full of 0.01 M Phosphate Buffer Saline (PBS buffer), pH 7.4, available from Sigma Chemical. The aldehydic silica was then incubated with 3.41 mg of protein A in PBS buffer overnight.

The column was then allowed to drain into a test tube, the volume noted, and the absorbance of the supernatant at 280 nm and 320 nm was noted. The column was then washed with 1 mL of PBS buffer. The wash was collected and the volume recorded, as well as, the absorbances at 280 nm and 320 nm. The wash procedure was repeated with fresh PBS buffer until there was no significant absorbances recorded at 280 nm or 320 nm, insuring that no unbound protein A was present. The amount of protein A present in the washes and supernatant was determined as follows:

mg in solution=(($A_{280}$−$A_{320}$)/0.14)×volume solution $A_{280}$=Absorbance at 280 nm $A_{320}$=Absorbance at 320 nm 0.14=Extinction coefficient ($E^{0.1}$%) of protein A The absorbance at 320 nm represents light scattering due to the presence of particles, notably silica, in the solution. These particles will also cause absorbance at 280 nm. Protein A has a strong absorbance at 280 nm, but little to no absorbance at 320 nm. By subtracting the absorbance at 320 nm from the absorbance at 280 nm, a true value of the absorbance due to protein A is obtained.

The amount of protein A bound to the silica was calculated by subtracting the amount of protein A collected in the supernatant and washes from the amount of protein A originally loaded on the columns (3.41 mg). Four samples of the derivatized silica produced in Example 1 were used and yielded the results shown in TABLE 2.

TABLE 2

| Sample | Protein A loading |
|---|---|
| 1 | 1.59 mg |
| 2 | 1.50 mg |
| 3 | 1.51 mg |
| 4 | 1.56 mg |
| average | 1.54 mg |

The standard deviation of the four trials was 0.04 mg and the coefficient of variation was 2.60%. These values demonstrate the successful attachment of protein A to the derivatized aldehydic silica.

EXAMPLE 4

The activity of the protein A columns was confirmed by qualitative enzymatic assay. A sample of 0.2 mg of peroxidase conjugated rabbit IgG whole molecule, available from Rockland, was diluted in 2 mL of cool 0.01M phosphate, 0.5M NaCl PBS coupling buffer. The enzyme solution was added to the protein A columns. A negative control consisted of the enzyme solution added to 0.4 mL of the derivatized silica without protein A attached. The protein A columns and the control were then incubated for 1.5 hours at 4° C. with gentle end-to-end mixing.

After incubation, the columns were drained and washed with PBS buffer. The washes were collected and the absorbances at 320 nm and 280 nm read. The columns were washed until there was no significant absorbance at either 280 nm or 320 nm, ensuring that no unbound conjugated IgG remained.

Next, 2.90 mL of 9.1 mM 2,2'-Azino-bis(3-Ethylbenzthiazoline-6-sulfonic Acid)(ABTS) in 100 mM potassium phosphate buffer, pH 5.0, and 0.05 mL of 0.3% (w/w) hydrogen peroxide solution in deionized water, were added to each of the columns. Peroxidase will catalyze the following reaction:

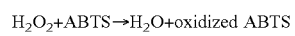

$H_2O_2$+ABTS→$H_2O$+oxidized ABTS

Oxidation of ABTS causes the development of a dark blue color, caused by an increase in the absorbance at 405 nm. During the qualitative assay, the protein A columns displayed instant and intense color development, while the negative control showed only an extremely slight color change over several minutes. The intense blue color in the protein A columns indicates the presence of bound active peroxidase conjugated IgG. The slight color change in the control is most likely due to minute amounts of peroxidase conjugated IgG that was nonspecifically bound to the aldehydic silica and not removed by the repeated washes.

EXAMPLE 5

Example 1 was repeated using 4% cross linked agarose in place of silica. Two duplicate samples of agarose were derivatized following the same general methodology as in Example 1, with the following modifications; 1)samples of 4% cross linked agarose were used in place of silica, 2) the samples were suspended in 50 mL of hexanes, 3) 20 mL of hexanes were added 3 hours into the reaction, 4) after the addition of the siloxane, the reaction was allowed to run 2 hours.

Organic loading testing could not be performed with agarose. Binding of protein A to the derivatized agarose was performed on columns containing 0.5 mL of derivatized agarose. Protein A loading values of 1.53 and 1.34 mg of protein A per 0.5 mL of derivatized agarose were obtained.

The forgoing examples demonstrate the successful binding of aldehydic alkoxy silanes to solid support matrix materials to produce a derivatized aldehydic matrix material. Also demonstrated is the successful binding of bio-molecules to the derivatized material.

It will be apparent to those skilled in the art that the invention of the present application is applicable to uses other than those demonstrated above. It is recognized that a wide variety of solid support materials having surface hydroxyl groups, or capable of having hydroxyl groups introduced, can be used. Further, it is recognized that a wide variety of aldehydic alkoxy silanes can be used, and that the derivatized materials produced therefrom could be used with a wide variety of bio-molecules in a number of biological applications. Hence, all of these equivalents are considered within the scope of the current invention.

What is claimed is:

1. An aldehydic derivatized matrix material comprising,
    a support matrix material having a surface area, and a siloxane polymer coating bonded to at least a portion of said surface area, wherein,
    said siloxane polymer coating comprises a plurality of silicon atoms cross-linked to each other through Si—O bonds, said plurality of silicon atoms having organic substituents containing aldehydic functional groups bonded thereto, said organic substituents being represented by the formula R—CHO, wherein R is selected from the group consisting of $C_1$ to $C_{30}$ straight chain, branched and cyclic alkyl; $C_2$ to $C_{30}$ straight chain, branched and cyclic alkenyl; aryl; and a covalent bond.

2. An aldehydic derivatized matrix material according to claim 1, wherein said support matrix material is selected from the group consisting of glasses, agarose, silica, alumina, glass-coated ELISA plates, resin, nickel, aluminum, zinc and paramagnetic iron.

3. An aldehydic derivatized matrix material according to claim 1, wherein said cross linked siloxane polymer has the general formula:

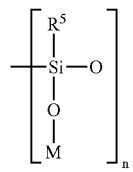

where M is the support matrix material, n is an integer from 1 to about 10,000 and $R^5$ is an organic substituent containing an aldehydic functionality.

4. A method for immobilizing bio-molecules, said method comprising:
    a) providing a column containing aldehydic derivatized matrix material comprising
       a support matrix material having a surface area, and a siloxane polymer coating bonded to at least a portion of said surface area, wherein,
       said siloxane polymer coating comprises a plurality of silicon atoms cross-linked to each other through Si—O bonds, said plurality of silicon atoms having organic substituents containing aldehydic functional groups bonded thereto, said organic substituents being represented by the formula R—CHO, wherein R is selected from the group consisting of $C_1$ to $C_{30}$ straight chain, branched and cyclic alkyl; $C_2$ to $C_{30}$ straight chain, branched and cyclic alkenyl; aryl; and a covalent bond;
    b) washing said column with a buffer;
    c) adding to said column a solution containing bio-molecules to be immobilized, and
    d) incubating said column to immobilize at least a portion of said blo-molecules.

5. A method according to claim 4, wherein said support matrix material is selected from the group consisting of glasses, agarose, silica, alumina, glass-coated ELISA plates, resin, nickel, aluminum, zinc and paramagnetic iron.

6. A method according to claim 4, wherein said siloxane polymer has the general formula:

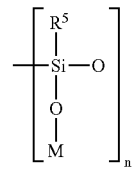

where M is the support matrix material, n is an integer from 1 to about 10,000 and $R^5$ is an organic substituent containing an aldehydic functionality.

7. An apparatus for immobilizing bio-molecules, said apparatus comprising,
    a hollow column, said column being adapted for receiving a matrix material to be filled into said column;
    an aldehydic derivatized matrix material disposed in said column, said derivatized matrix material comprising, a support matrix material having a surface area, and a siloxane polymer coating bonded to at least a portion of said surface area, wherein,
    said siloxane polymer coating comprises a plurality of silicon atoms cross-linked to each other through Si—O bonds, said plurality of silicon atoms having organic substituents containing aldehydic functional groups bonded thereto, said organic substituents being represented by the formula —R—CHO, wherein R is selected from the group consisting of $C_1$ to $C_{30}$ straight chain, branched and cyclic alkyl, $C_2$ to $C_{30}$ straight chain, branched and cyclic alkenyl, aryl and a covalent bond.

8. An apparatus according to claim 7, wherein said hollow column has a top end and a bottom end, said top end being open for receiving said matrix material, and said bottom end having a fitted plug, said fitted plug having a porosity such that said fitted plug permits the exit of fluids from said hollow column.

9. An apparatus according to claim 7, wherein said hollow column is a microtube, said microtube having a top end and a bottom end, said top end having an opening and a cap, and said microtube being generally adapted for use with a centrifuge.

10. An apparatus according to claim 7, wherein the hollow column can accommodate a raw solid support matrix material, an aqueous acid and an alkoxy aldehydic silane.

11. An apparatus according to claim 7, wherein said support matrix material is selected from the group consisting of glasses, agarose, silica, alumina glass-coated ELISA plates, resin, nickel, aluminum, zinc and paramagnetic iron.

12. An apparatus according to claim 7, wherein said siloxane polymer has the formula:

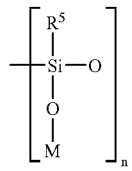

where M is the support matrix material, n is an integer from 1 to about 10,000 and $R^5$ is an organic substituent containing an aldehydic functionality.

13. The aldehydic derivatized matrix material according to claim 1, wherein:

said siloxane polymer coating is a multi layer siloxane polymer and the placement of individual silicon atoms in said polymer is random with respect to said support matrix material.

14. The method according to claim 4, wherein:

said siloxane polymer coating is a multi layer siloxane polymer and the placement of individual silicon atoms in said polymer is random with respect to said support matrix material.

15. The apparatus according to claim 7, wherein:

said siloxane polymer coating is a multi layer siloxane polymer and the placement of individual silicon atoms in said polymer is random with respect to said support matrix material.

* * * * *